US00PP13456P2

(12) United States Plant Patent
Bradford

(10) Patent No.: US PP13,456 P2
(45) Date of Patent: Jan. 7, 2003

(54) NECTARINE TREE NAMED 'SWEET SURPRISE'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,021

(22) Filed: Dec. 13, 2001

(51) Int. Cl.[7] ..... A01H 5/00
(52) U.S. Cl. ..... Plt./192; Plt./190
(58) Field of Search ..... Plt./190, 192

(56) References Cited

U.S. PATENT DOCUMENTS

PP7,193 P 3/1990 Bradford ..... Plt./190
PP11,954 P2 6/2001 Bradford ..... Plt./190

*Primary Examiner*—Bruce R. Campell
*Assistant Examiner*—W C Haas

(57) ABSTRACT

The present invention relates to a nectarine tree, *Prunus persica*, and more particularly to a new and distinct variety broadly characterized by a large size, vigorous, hardy, self-fertile, productive and regular bearing tree. The fruit matures under the ecological conditions described approximately the first week in July, with first picking on Jul. 6, 2001. The fruit is uniformly large in size, subacid in flavor, globose in shape, freestone in type, firm in texture, yellow in flesh color, and red in skin color. The variety was developed as a first generation cross using 'Red Glen' (U.S. Plant Pat. No. 7,193) yellow flesh nectarine as the selected seed parent and an unnamed white flesh nectarine as the selected pollen parent.

1 Drawing Sheet

CROSS REFERENCE TO RELATED APPLICATIONS

This case is related to co-pending U.S. Plant patent application Ser. No. 10/014,020, filed Dec. 13, 2001, drawn to 'SWEET PEARL' nectarine.

BOTANICAL CLASSIFICATION

*Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'SWEET SURPRISE'. The present variety was hybridized by me in 1992, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Red Glen' (U.S. Plant Pat. No. 7,193) yellow flesh nectarine as the selected seed parent and an unnamed white flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Red Glen' (U.S. Plant Pat. No. 7,193) nectarine, by producing nectarines that are globose in shape, firm in texture, and almost fully red in skin color, but is distinguished therefrom and an improvement thereon by producing fruit that is freestone instead of clingstone, that is subacid instead of acid in flavor, and that matures about three weeks earlier.

The present variety is most similar to 'Grand Sweet' (U.S. Plant Pat. No. 11,954) nectarine by producing nectarines that are subacid and sweet in flavor and full red in skin color, but is distinguished therefrom and an improvement thereon by producing fruit that is freestone instead of clingstone, that matures about two weeks earlier, and that has a sweet instead of bitter tasting kernel.

DRAWING

The accompanying photograph exhibits four whole fruits positioned to display the characteristics of the skin color and form, one fruit divided around the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin County), Calif., and was developed at the state of firm ripe on Jul. 9, 2001, on the original tree during its ninth growing season. All major color code designations are by reference to the Inter-Society Color Council, National Bureau of Standards. Common color names are also used occasionally.

Tree

Size: Large, reaching and maintaining a height of 14' [4.27 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Stocky, reaching a maximum diameter of 7" [178 mm.] after the ninth growing season.
*Texture.*—Shaggy.
*Bark color.*—Grayish yellowish brown [80. gy.yBr].
*Lenticels.*—Numerous. Color: Moderate orange yellow [71. m.OY]. Average Size: ¼" [6.4 mm.].
Branches:
*Size.*—Diameter of scaffold is 3½" [89 mm.] measured 12" above the crotch, typical of *Prunus persica*, and dependent upon cultural practices and climatic conditions.
*Texture.*—Smooth on 1st year wood, increasing to rough with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Numerous. Color: Light orange yellow [70. l.OY]. Average Size: Small, 1/16" [1.6 mm.].
Leaves:
*Size.*—Large. Average Length: 6¼" [159 mm.]. Average width: 1½" [38 mm.].
*Arrangement.*—Alternate.
*Thickness.*—Medium.
*Form.*—Elliptical.
*Apex.*—Acuminate.
*Base.*—Acute with an average angle of 70 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: 7/16": [11.1 mm.]. Average Thickness: 1/16" [1.6 mm.]. Color: Brilliant yellow green [116. brill.YG].
*Stipules.*—Number: 2 per leaf, up to 6 per growing tip. Average Length: ¼" [6.4 mm.]. Color: Light yellow green [119. l.YG] when growing.
*Glands.*—Number: 2 to 6. Position: Both alternate and opposite, positioned both on the petiole and base of the leaf blade. Size: Small. Form: Reniform. Color: Brilliant yellow green [116. brill.YG].
*Leaf buds.*—Pointed.
Flower buds:
*Hardiness.*—Hardy, with respect to central California winters.
*Diameter.*—Typically ⅜" [9.5 mm.] 1 week before bloom.
*Length.*—Typically ¾" [19.1 mm.] 1 week before bloom.
*Form.*—Not appressed.
*Surface.*—Pubescent.
*Color.*—Light purplish pink [249. l.pPk].
Flowers: Perfect, complete, perigynous, usually a single pistil, typically thirty or more stamens, five sepals and petal locations alternately positioned.
*Type.*—Showy.
*Average flower diameter.*—1¾" [44.5 mm.].
*Number of petals.*—Usually five, rarely more.
*Petal shape.*—Rounded.
*Petal margin.*—Wavy.
*Average petal diameter.*—¾" [19.1 mm.].
*Average petal length.*—¾" [19.1 mm.].
*Petal apex.*—Rounded.
*Petal base.*—Rounded, very wavy.
*Petal color.*—Pale purplish pink [252. p.pPk].
*Anther color.*—Moderate red [15. m.R].
*Stigma color.*—Light greenish yellow [101. l.gY].
*Sepal color.*—Dark purplish red [259. d.pR].
*Sepal length.*—3/16" [5 mm.].
*Sepal width.*—3/16" [5 mm.].
*Average pistil length.*—⅝" [15.9 mm.].
*Average stamen length.*—11/16" [17.5 mm.].
*Fragrance.*—Moderate when nectar is present.
*Blooming period.*—Late when compared with other varieties.
*Onset of bloom.*—One percent on Mar. 7, 2001.
*Date of full bloom.*—Mar. 14, 2001.
*Duration of bloom.*—One to two weeks, dependent on ambient temperature.
*Number per cluster.*—Generally 1 to 2, rarely more than 2.

FRUIT

Maturity when described: Hard ripe, Jul. 9, 2000.
Date of first picking: Jul. 6, 2000.
Date of last picking: Jul. 20, 2000.
Size: Uniform, large.
*Average diameter axially.*—2⅞" [73 mm.].
*Average diameter across suture plane.*—2¾" [70 mm.].
*Typical weight.*—6.1 ounces [173 grams].
Form: Uniform, somewhat asymmetrical, globose.
*Longitudinal section form.*—Roundish.
*Transverse section through diameter.*—Roundish.
Suture: An inconspicuous line extending from the base to the pistil point becoming a shallow groove near the apex and having a marked depression just beyond the pistil point.
Ventral surface: Rounded, lipped toward the apex on both sides.
Lips: Slightly unequal.
Cavity: Flaring, elongated in the suture plane, suture showing on both sides, Brilliant orange yellow [67. brill.OY] stem markings typical.
*Depth.*—½" [12.7 mm.].
*Breadth.*—13/16" [20.6 mm.].
Base: Truncate.
Apex: Rounded.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Texture.*—Smooth.
*Tenacity.*—Tenacious to flesh.
*Astringency.*—Nonastringent.
*Tendency to crack.*—None observed.

*Color.*—Very deep red [14. v.deep R] over a Strong reddish orange [35. s.rO] background color with some Light orange yellow [70. l.OY] freckling on the cheeks toward the apex.

Flesh:

*Color.*—Brilliant yellow [83. brill.Y] from skin to within 1/8" [3.2 mm.] of the stone, with some Dark red [16. d.R] streaking close to the stone.

*Surface of pit cavity.*—Dark red [16. d.R] fibers cleanly detaching from the stone.

*Amygdalin.*—Scarce.

*Juice.*—Abundant, rich.

*Texture.*—Firm, crisp.

*Fibers.*—Abundant, fine.

*Ripens.*—Slightly earliest at apex and along the cheeks.

*Flavor.*—Subacid and sweet, ranging from 15 to 16 brix.

*Aroma.*—Moderate.

*Eating quality.*—Very good.

STONE

Type: Freestone.
Average width: 1 1/16" [27.0 mm.].
Average length: 1 1/2" [38.1 mm.].
Average breadth: 3/4" [19.1 mm.].
Average pit wall thickness: 1/4" [6.4 mm.].
Form: Oval.
Hilum: Narrow.
Base: Slightly oblique.
Apex: Acute, with a 1/8" [3.2 mm.] tip forming an angle of 45 degrees.
Side: Equal.
Surface: Irregularly furrowed near the apex and pitted toward the base.
Ridges: Jagged toward the base.
Color: Moderate brown [58. m.Br].
Tendency to split: None observed.
Kernel:

*Form.*—Oval.

*Pellicle color.*—Grayish brown [61. gy.Br].

*Skin color.*—Light yellow [86. l.Y] when first removed.

*Vein color.*—Deep brown [56. deep Br].

*Taste.*—Sweet.

*Viable.*—Yes.

*Average width.*—7/16" [11.1 mm.].

*Average length.*—3/4" [19.1 mm.].

*Amygdalin.*—Scant.

USE

Market: Fresh market, long distance shipping, backyard grower.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Grand Sweet' (U.S. Plant Pat. No. 11,954) nectarine by producing nectarines that are subacid and sweet in flavor and full red in skin color, but is distinguished therefrom and an improvement thereon by producing fruit that is freestone instead of clingstone, that matures about two weeks earlier, and that has a sweet instead of bitter tasting kernel.

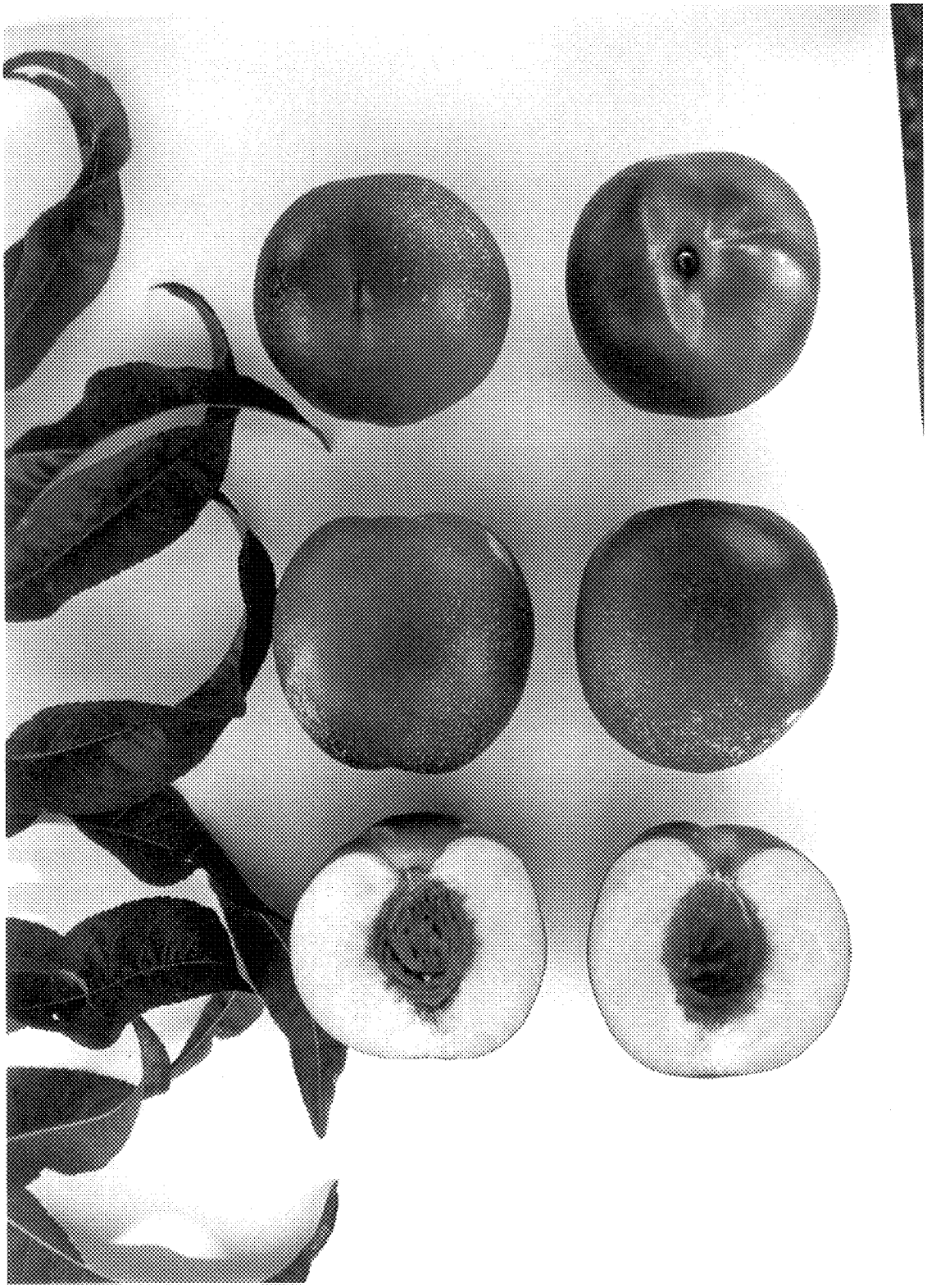

* * * * *